United States Patent [19]

Roberts

[11] 4,035,917
[45] July 19, 1977

[54] REINFORCING DENTAL PIN CUTTER AND RETAINER

[76] Inventor: James Norman Roberts, 32206 Old Forge Lane, Farmington Hills, Mich. 48024

[21] Appl. No.: 643,850

[22] Filed: Dec. 23, 1975

[51] Int. Cl.² .............................................. A61C 3/00
[52] U.S. Cl. .................................................... 32/40 R
[58] Field of Search ................... 32/40; 128/318, 305, 128/321

[56] References Cited

U.S. PATENT DOCUMENTS

| | | | |
|---|---|---|---|
| 1,471,422 | 10/1923 | Shearer | 128/321 |
| 1,676,574 | 7/1928 | Ostermeier | 128/313 |
| 2,751,908 | 6/1956 | Wallace | 128/321 |
| 3,754,331 | 8/1973 | Agnone | 32/40 R |
| 3,895,636 | 7/1975 | Schmidt | 128/305 |

*Primary Examiner*—G.E. McNeill
*Attorney, Agent, or Firm*—Sixbey, Bradford & Carlson

[57] ABSTRACT

An instrument, especially useful in the field of dentistry by virtue of its shape, size, and construction, adapted for example for severing ends from threaded retention pins which have been inserted intra-coronally in natural teeth to aid in retentively adhering tooth restoration material to a tooth being repaired, and operable subsequent to such severance to positively contain a severed end for facile removal thereof from a patient's mouth. The instrument has additional uses in, as one example, the field of intra-oral surgery of a type that includes utilization of wire arch bars in a procedure to immobilize a patient's jaws, where jaw fracture exists, and after placement and affixation, wire ends can be severed and retained by the instrument for removal from the mouth of the patient. The instrument can also be used in the field of orthodontics to, for example, trim or cut wire ends and remove the so-severed wire ends. The instrument while capable of other usages, is primarily useful for operation in small and restricted, or difficult access areas, due to its relatively small dimensions and its shape, coupled with the facile and effective operation thereof, particularly for the severing and retention of wire ends and the like such as encountered in the use of threaded retention pins as aforesaid.

12 Claims, 17 Drawing Figures

U.S. Patent   July 19, 1977   Sheet 1 of 2   4,035,917
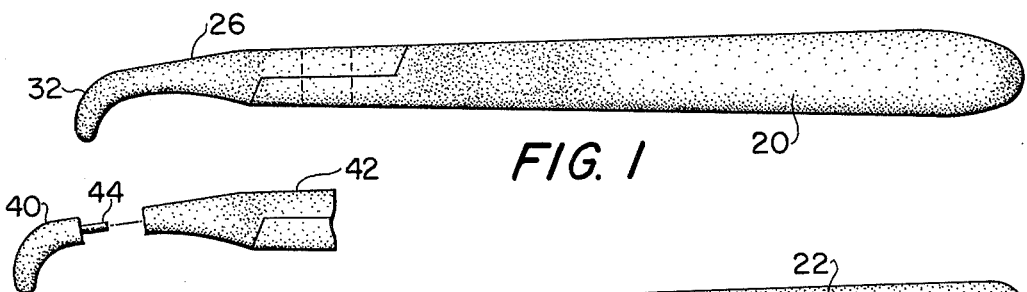
FIG. 1
FIG. 1A
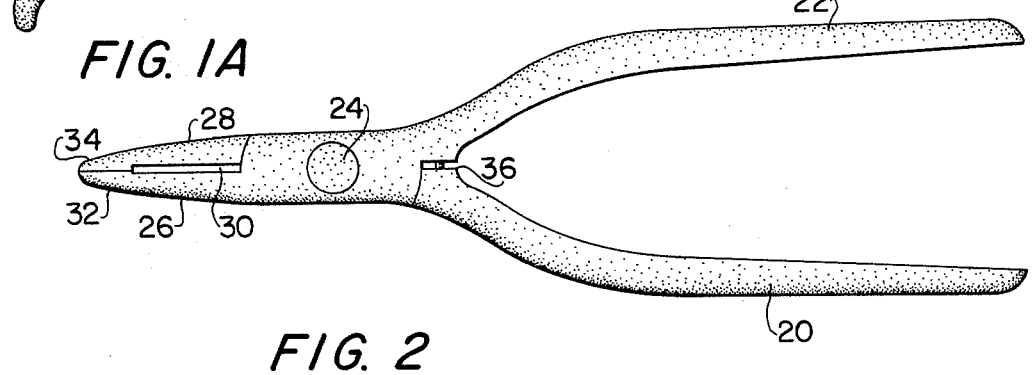
FIG. 2
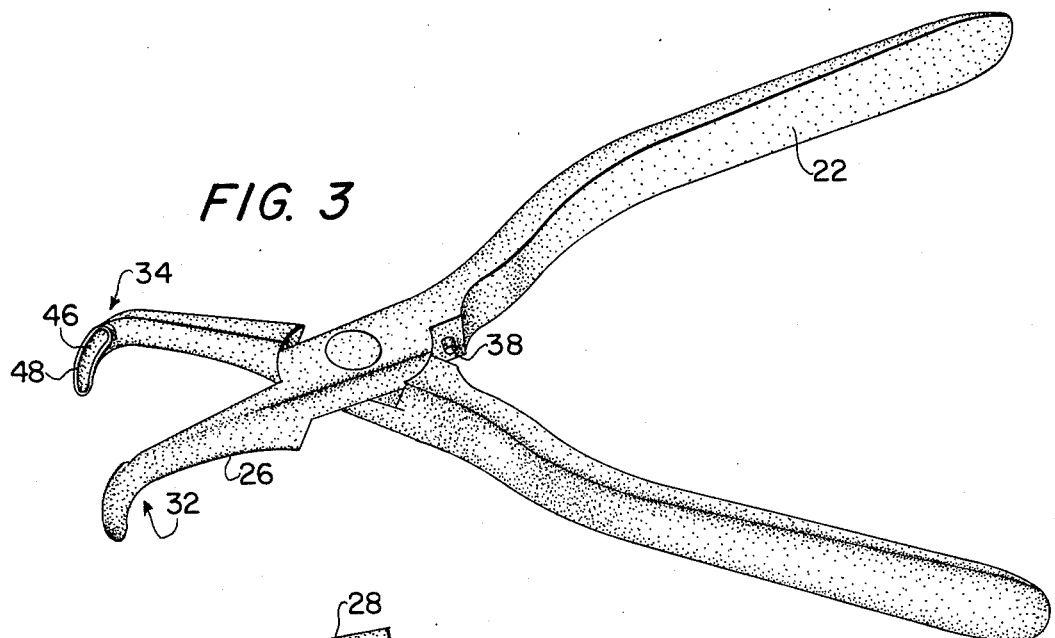
FIG. 3
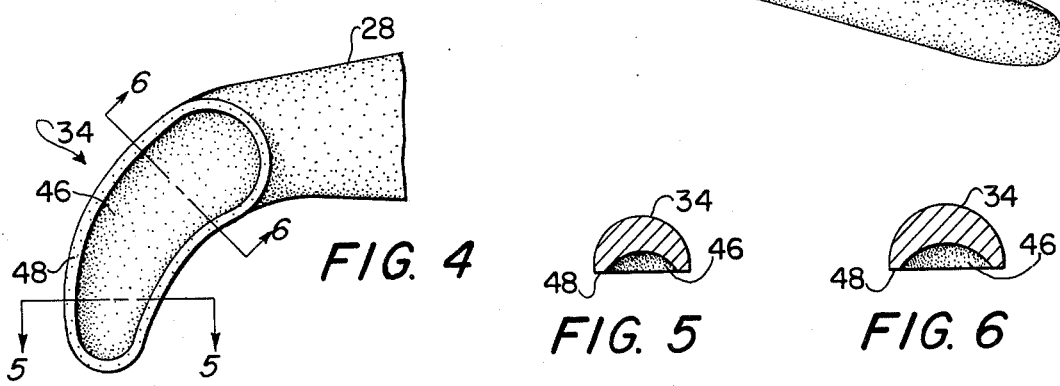
FIG. 4
FIG. 5
FIG. 6

REINFORCING DENTAL PIN CUTTER AND RETAINER

BACKGROUND OF THE INVENTION

Heretofore in the practice of dentistry, steps have been taken to restore teeth which have either been broken or decayed. One of the known and heretofore practiced methods has been to utilize so-called retention pins which are threaded and/or otherwise provided with external surfaces to aid retention in a tooth and which have flattened head portions thereon. The practice included removal of the decayed or broken portions of a tooth to be restored, drilling of bores or holes in the remaining tooth structure, inserting threaded or the like retention pins in such holes or bores in the natural tooth intra-coronally, placement of restorative material in the desired area, shaping and dressing of the restorative material and in some instances placing a cap or the like on the so-restored tooth.

As is known in the art the utilization in the intra-coronal space or area of a tooth limits to a substantial extent access and use of practical instruments and this is especially applicable where such retention pins after placement are to be severed to the desired extending length which remains projecting from the natural tooth. Another method consists in the retention pins being cut to size externally of a patient's mouth and then put in place, and generally is applicable to the old Markley type which is cut to size and then cemented in place. The present invention permits placement of a retention pin such as a stainless steel threaded pin having a flattened head thereon in a drilled bore intra-coronally of a tooth which has been prepared for reception in the bores of these pins and subsequently the pins can be cut to length by means of the present invention and the so-cut end can be retained by the invention for removal from the mouth of the patient. No known tool exists providing positive retention of the cut particle to prevent aspiration or ingestion by the patient or preventing eye injury to the clinician.

STATEMENT OF THE INVENTION

The present invention provides a new and novel design, practicality, and efficiency for the specific function for which designed. The present invention is in the nature of a plier type cutter and of such dimensions and shape to provide a conceptually different instrument for a specialized function which basically includes cutting and capturing in a closed compartment a cut end of a stainless steel pin placed intra-coronally in bores provided in a shaped natural tooth portion and which pin is not of uniform diameter but contains a head. While the present invention, to a certain extent, includes a combination of known physical and geometric principles and design it is for a specific function not heretofore harmoniously united for that purpose. That purpose is to cut and capture in a closed compartment the cut end of a stainless steel pin placed intra-coronally and not of totally uniform diameter but containing a head; the invention to be used in such small intra-coronal space limitations in the nature of 2-4 millimeters in extent.

For purposes of use in such intra-coronal areas the instrument must have a pre-established configuration and dimensions which permit insertion between such retention pins and the instrument must meet the requirement of having a small extent of cutter end separation because of this very small operating space available to open the instrument and engage and cut the stainless steel retainer pins, in many instances this dimension being in the nature of 2.5 millimeters.

The plier type cutter includes two arms pivotally mounted one to another and having jaws on the ends of the arms, the pivot point and lengths of the arms and jaws being such as to provide for a positive cutting action of retention pins while at the same time of sufficiently small dimensions to permit placement and use within the restricted areas. The cutting jaws as will be defined hereinafter include cupped cutting tips to sever the retention or reinforcing pin by a cutting action of the cup edges and coacting cup edges on each of the jaws at the ends of the arms form, subsequent to cutting of the end from the pin, a closed cup to entrap and to retain the cut end in the cup depression.

In an embodiment of the invention a neoprene or other material insert is placed between the two arms or handles to bias the pliers or cutter instrument to a slightly open position. The pins utilized have a diameter of approximately one-half millimeter and a flattened head parallel to the axis of the pin having a maximum width across the head of 0.8 millimeters. As will be set forth hereinafter the total width across the cutting tip is approximately 3 millimeters or 0.12 inches and one-half of the cutting end at the tip is approximately 1½ millimeters.

In one form of the invention a compressive cut between two substantially flat members is contemplated while in a second embodiment one of the cutting tips can have a raised or sharpened cutting edge to coact with a flat compressive cutting edge from the other tip portion. Preferably the cutter tip having the sharpened edge has this sharpened edge portion extending through approximately 180° so that the pliers can be utilized at different angles to accommodate to different oral positions and to different alignments of the retention pins in the teeth.

Basically there are certain essential features which must be provided in order to render the instrument practical and which result in a new, novel and patentable construction as compared with prior known art and instruments. These essential features include the overall configuration; handles or arms pivoted at a point to provide a sufficient cutting force to the cutting edges at the ends of jaws at the opposite side from the pivoted handles; the jaws must have an angular disposition with respect to the handles or arms for intra-coronal access of the cutting tips and which results from the jaws being at a substantial angle to the longitudinal axis of the arms and preferably of a curvilinear nature; the jaws have small dimensions and form a cup therebetween to permit intra-coronal access; angular movement or separation of the jaws must be small but sufficient to encompass a wire between opposed cutting edges; and the cup formed by closed cutting edges must be operable to retain the cut end of the pin for removal from a patient's mouth.

To effect these end results the device can be so deviated or angularly positionally disposed in conjunction with the cutting edges extending over 180° of the cutting jaws to permit cutting of the pins arranged at various angular positionments or positions intra-coronally. The interconnected handles of substantial length are pivotally interconnected proximate shorter jaws, as relates to jaw length, with the fulcrum near the cutting tip to reduce arm flexure and produce greater cutting force. The jaws are angularly extended from the respective handles, beyond the point of pivot, in a plane at right angles to the plane of displacement or movement of the handles and jaws and the thickness of each jaw portion is approximately 1.5 millimeters. The cup portions on each half of the composite jaw in operation is in the nature of, preferably, an elongated oval shape and contain thereon active cutting edges or tips and jointly defining therebetween with the tips in a closed coacting relationship a retaining compartment or cup for the severed end of the pin. The cutting edges are formed by cupping out or recessing the cutting tips and the cutting edges in effect are the peripheral mating edges so formed and adapted for cutting interengagement with respect to and through a retention pin.

The present instrument is utilizable in connection with amalgam type of restoration of the tooth by surrounding the area to be restored with an enclosing band in a usual known manner and with the retention pins in place intra-coronally, then packing the area within and defined by the enclosing band with amalgam like filling of a cavity with an exposed exterior surface with the pins retaining and reinforcing the amalgam as placed in position on the remaining natural tooth. The same principle is utilized in large cavities where pins are used as strengthening, reinforcement and means to prevent lateral movement of the amalgam fillings packed therein.

It will be seen from the following description of an embodiment of the invention in conjuction with its use in tooth restoration that a clinical crown can be to a large extent restored with amalgam to present a typical restorative core ready for crown preparation by redressing and shaping of the restorative material.

It will also be apparent from the following description that the present instrument is extremely facile as regards its placement and use in the mouth of the patient and with respect to the placement and treatment of retention pins placed intra-coronally of the tooth. Due to the configuration and dimensions, the pin channel and pin can be placed at angles parallel to the external enamel wall in certain types of tooth restoration, and a pin when placed and bent to an angle parallel with the long axis of the tooth is still possible and permits placement of the pin in a manner to assure seating of the pin in the dentin and not in the enamel. Bending allows for a lateral bulk of restorative material. The pin is then cut off about 1½ millimeter to allow for a bulk and strength of overlying material incisally.

Many other advantages and features of the present invention will become more readily apparent from the following detailed description of an embodiment thereof when taken together with the accompanying drawings in which:

FIG. 1 is a side view of the instrument of the present invention;

FIG. 1a is a fragmentary view of a modified form of the instrument of FIG. 1 including a removable cutting tip portion;

FIG. 2 is a plan view of the instrument of FIG. 1 in closed position;

FIG. 3 is a view of the instrument in an open position wherein the handle and jaws are displaced by rotation around the pivot point and including a showing of resilient or elastic initial spreading means between the handles or arms;

FIG. 4 is an enlarged fragmentary detail view of the cutting tip on a jaw as seen in the upper jaw of FIG. 3 and showing in greater detail the cutting edge and partial depression in the edge for partial formation of a retention cup;

FIG. 5 is a sectional view taken on line 5—5 of FIG. 4 showing in detail the configuration at that position of the cutting tip;

FIG. 6 is a sectional view taken on line 6—6 of FIG. 4 showing details at a different position of the cutting tip;

Figure 10:
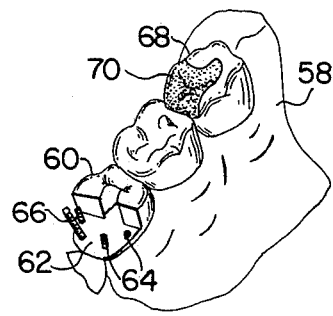
Figure 11:
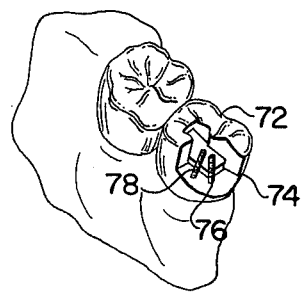
Figure 12:
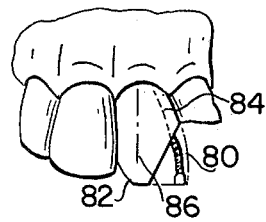
Figure 13:
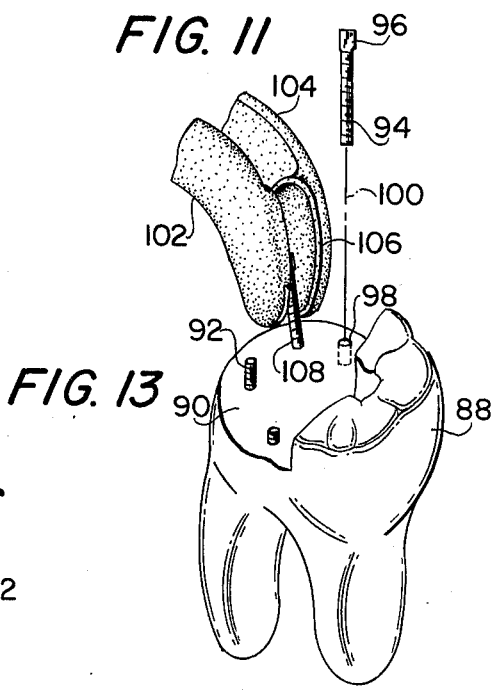
Figure 14:
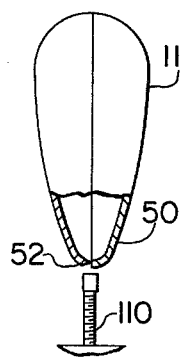
Figure 15:
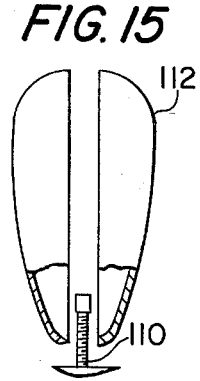
Figure 16:
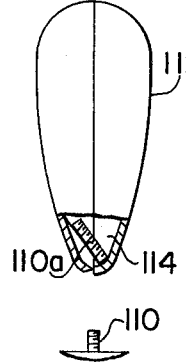

FIG. 10 is a fragmentary view of a portion of a jaw of a patient having teeth therein and disclosing a restorative process as applied to a lower right first molar wherein a portion of the natural tooth has been removed and retention pins placed in bores or holes therein with some of the ends of the pins having been removed and with the back molar having been 60% restored by amalgam and forming a typical completed core ready for crown preparation;

FIG. 11 shows a jaw portion including a lower left second molar with retention pins in position therein and angularly disposed for purposes to be defined;

FIG. 12 is a fragmentary view of the jaw portion wherein the upper left central incisor has a portion of the tooth removed and disclosing the pin after placement bent to an angle parallel with the longitudinal axis of the tooth for practical purposes of tooth restoration;

FIG. 13 is a composite view showing a tooth being restored or repaired and having retention pins mounted in bores therein and with the cutting tips of the present instrument in cutting position for cutting off the end of the pin for removal from the mouth of the patient by entrapment within the cavity formed by the mating ends;

FIGS. 14, 15 and 16 are diagrammatic views of portions of the jaw ends or cutting tips disclosing a tip configuration in which tip portion is sharpened to a point to facilitate cutting and the views respectively showing the cutting tip being positioned adjacent a retention pin; opened and surrounding the end of the retention pin and the end of the retention pin subsequent to removal thereof by cutting being entrapped or held within the closed mating ends in the entrapment compartment formed thereby.

Referring now in detail to the drawings, the instrument includes, in a manner similar to plier constructions, opposed handle portions 20 and 22 pivotally interconnected by means of a pivot at 24 and it will be noted that this pivot is arranged with respect to jaw portions 26 and 28 so as to provide ample cutting engagement between the cutting surfaces and at the same time prevent too substantial a lateral bending or stressing of the handle portions. The jaws 26 and 28 as shown in FIG. 3 for example are formed as extensions of the handle portions in a usual manner and in closed position are provided with an opening generally designated 30 (FIG. 2) formed by removal of a portion of the opposing jaw surfaces for the purpose of facilitating formation of cutting tip portions generally designated 32 and 34, the clearance permitting extension of the actual cutting or clipping portions and to permit sufficient cutting force during flexure of the jaw portions therebetween. The opening 30 can be rectilinear or tapered toward the extreme edges if desired. It will also be noted from FIGS. 2 and 3 that the handle portions aft of pivot 24 are so cut as to provide an opening generally designated 36 therebetween and in which, secured to one handle interior, for example handle portion 22, a resilient insert 38 which serves to bias the two handle portions to a slightly open position. This neoprene rubber insert is squeezed during a cutting operation and will return to its original shape upon release of pressure on the handle portion to permit withdrawal of a cut wire end from the retaining cup as will appear hereinafter. The handle portions can preferably be chrome plated but need not consist of hardened steel and the actual formation thereof is not of the essence provided that the configuration and length are such as to permit insertion and manipulation of the instrument and especially the cutting edges or tips into an appropriate and operative position.

Attention is also drawn to FIG. 1a in which the end of the jaw portion as indicated at 40 is removable from the handle portion 42, the jaw having a rearward pin 44 insertable in a mating opening, not shown, in handle 42 and thereby providing a structure with a removable jaw portion with appropriate means being provided for retention of the removable end.

The cutting tip portions generally referred to as 32, 34, and as generally alluded to hereinbefore have at their tips recessed portions or areas formed therein such as indicated for example in FIGS. 3 and 4 at 46. These cupped out areas are so devised and formed as to provide peripheral cutting edges 48 which surround the cupped out or cavity 46 portion and the peripheral edge 48 in its lower portion being substantially elliptical in shape. The actual configuration of the cupped out portion and cutting edges will be more readily apparent from a study of FIGS. 5 and 6. In this embodiment it is to be noted that the edges 48 are flat and serve as compressive cutting edges with respect to a corresponding opposing jaw as will be readily apparent.

The functions of these cutting tips and cavities are more readily apparent from FIGS. 14, 15 and 16 wherein in FIG. 15 the jaws have been opened to surround the retention pin and in FIG. 16 an end portion of the retention pin has been clipped off and is confined or contained in the cavity chamber formed between the two end portions for removal from a patient's mouth in an apparent manner.

Figure 7:
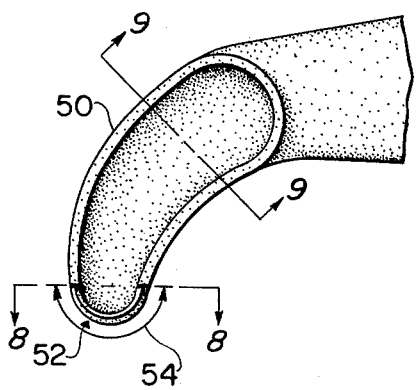
FIG. 7 is an enlarged fragmentary detailed view similar to FIG. 4 illustrating a modified cutting tip configuration having a sharpened end area extending over substantially 180° to facilitate and improve the cutting action.
Figure 8:
FIG. 8 is a sectional view taken on line 8—8 of FIG. 7.
Figure 9:
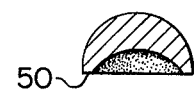
FIG. 9 is a view taken on line 9—9 of FIG. 7.

FIGS. 7, 8 and 9 show a modified form of the cutting tips. Here the cutting edges for the portion 50 are flat similar to the edge 48 of FIG. 4 but the end portion generally designated 52 is beveled through 180° as indicated by the arc and arrows 54 to form a cutting pointed edge 56 for engagement with an opposed flattened edge on the coacting jaw or which if desired could also be flattened. The remainder of the structure in these Figures is identical to the preceding described one.

As more specifically set forth in relationship with the description of the individual Figures, the use of the present invention is more readily understandable from a study of FIGS. 10-16 inclusive. In FIG. 10 for example a lower right jaw section is shown at 58 and as specifically shown the first molar 60 has a portion shown at 62 removed for restorative purposes. A plurality of retention pins 64 are shown inserted in bores or openings formed in the remaining natural tooth portion and the ends of these pins 64 have been cut off or removed as will be described later. The pin as shown at 66 has not as yet had its end removed. It is also interesting to note in this Figure that the pins 64 are spaced approximately 2-3 millimeters apart and as pointed out hereinabove each of the cutting jaws is approximately 1.5 millimeters in thickness so as to provide an area for insertion between the retention pins. This Figure also shows the rear molar 68 which has been approximately 60% restored by use of silver amalgam shown at 70 of a usual type and this tooth is an example of one typically completed with the core ready for crown preparation. The amalgam can be placed in the usual manner and with the utilization of retention pins to facilitate and prevent movement with respect to the remainder of the tooth.

In FIG. 11 there is shown the lower left jaw portion wherein the second molar 72 has been partially removed as shown at 74 and the retention pins shown at 76 have had their heads removed and particular attention is directed to pin 78 which is set at an angle to the remainder of the tooth so as to stay within the normal confines of the enamel portion encasing the tooth before decay and to facilitate proper restoration of the tooth. The configuration, dimensions, etc. of the instrument permit utilization within this confined area for clipping or cutting of the pin ends.

In FIG. 12 the pin 80 with the head still thereon is placed in an upper left central incisor 82 which after insertion in the straight bore 84 indicated by broken lines is bent to an angle parallel with the longitudinal axis of the tooth as indicated by the broken line at 86. This pin after placement as above expressed is cut off at about 1½ millimeters to allow for bulk and strength of overlying material incisally. This is a recognized practice but the present invention permits easy access and operation in this regard.

In FIG. 13 a tooth 88 has a removed portion 90 and pins such as indicated at 92 inserted in bores therein. This step is diagrammatically illustrated by showing of the overall pin 94 with its head 96 to be inserted in bore or opening 98 as indicated by broken line 100 and thereafter the end will be severed as schematically shown by opposing jaws 102 with their cutting edges 106 surrounding the pin and when the handle portions are brought together under force the upper end of this pin 108 will be cut and retained in the retaining cavity formed between mating and coacting cutting edges. This latter is schematically shown in FIGS. 14-16. In FIG. 14 the pin 110 is in position in the tooth and the instrument generally designated 112 has been brought into position for further or subsequent operation. In this embodiment the cutting edges are similar to that shown in FIG. 7 with the sharpened end 52 and flat section 50. The instrument in FIG. 15 has been opened and the jaws and cavities surround the upper end of the pin. In FIG. 16 the mating jaws 112 have been brought together by pressure on the handles and the pin 110 has had its upper end 110a cut therefrom and this end is retained in the cavity indicated 114 for removal from the patient's mouth.

As pointed out hereinbefore there are certain dimensions which are significant to permit utilization in the desired manner. For example the nose end portion of the cutting tips 32 has a radius of 0.12 inches with the radius of the inner curvature or lower curvature being 0.56 inches and the outer or upper curvature radius being 0.75 inches. The length from the bend to the straight aft portion of the jaw is approximately 0.85 inches and from thence to the useful rear portion of the handle approximately 4.5 inches. The thickness of each jaw portion where they mate initially is approximately 0.35 inches. The dimensions of the slot 30 (FIG. 2) varies from the leading edge at approximately 0.03 inches to 0.06 inches at the rear and extends over the length of approximately 0.75 inches. The clearance 36 is approximately 0.012 inches and the distance between the arm rear ends is approximately 1.75 inches. In the embodiment of FIGS. 4-6 the radius of the rear curvature of the opening defined by edge 48 is approximately 0.16 inches and the thickness of edge 48 is approximately 0.005 inches. The outer radius at section 55 is 0.15 inches and the inner radius 0.14 inches. The outer diameter or length at section 66 is 0.19 inches and the inner radius 0.18 inches.

In the embodiment of FIGS. 7-9 the 180° sharpened edge as at 52 extends for a distance of 0.12 inches. The inner radius at section 88 is approximately 0.04 inches and the outer radius approximately 0.07 inches. With these dimensions the functionality of the device is good.

Obviously if desired sharpened cutting edges can be provided bilaterally on the cutting tips rather than use of a cutting side and an anvil side as shown and described.

While the invention has been shown and described related to a preferred embodiment and use, obviously minor modifications and other uses will be apparent to other artisans, and the language of the accompanying claims is not to be so restrictively construed as to remove such from the protection afforded.

Manifestly minor changes in details can be effected without departing from the spirit and scope of the invention as defined in and limited solely by the appended claims.

I claim:

1. A dental instrument for cutting and severing end portions of metal wires, pins and the like, collecting severed cuttings as cut, and containing the collected cuttings for subsequent removal, said instrument being generally of a construction similar to pliers, including pivoted handle portions and cutting jaws at the ends of the pivoted handle portions, said instrument, and principally said cutting jaws, being of a shape, size, construction and configuration for coactive insertion thereof into small spaces in a human mouth wherein wire retention pins have been inserted intra-coronally in a bore in a natural tooth to aid in retentatively adhering and reinforcing tooth restoration material applied to the natural tooth being repaired, being insertable between said pins to selectively engage an end of a said pin to sever the same, or in intra-oral surgery of a type which also includes utilization of securement wire for arch bars in a procedure to immobilize a patient's jaws, where jaw fracture exists, or for cutting and trimming wire ends in orthodontic procedures, the shape, size, construction and configuration of the cutting jaws permitting insertion and engagement of the cutting jaws about said metal end portions in severely restricted areas to permit severing the wire ends, said cutting jaws each further including, on the inner side thereof, inward facing half cup recessions matable one with the other upon closure of the jaws to constitute a totally closed and sealed severed wire end retaining compartment for removal thereof from a mouth, said half cups having interacting and interengaging cutting edges formed on at least the forward free end edges of the cup recessions, said jaw ends being generally smoothly and continuously curvilinear, and being curved in a direction angled from the longitudinal axis of the handle portions at a substantial angle to the plane of opening of said arms, said recessions being formed in said curvilinear portions and of an elongated curvilinear generally oval shape corresponding to the shape of the jaw ends to facilitate the insertion and operation of the jaw ends within restricted areas of a human mouth, said instrument and the cutting and retaining action being operable in all positions of rotation of said instrument.

2. In an instrument as claimed in claim 1, said mating half cups on said jaw ends being formed by half cup shaped depressions in the material of the jaw ends and wholly contained in the thickness of said jaw ends for thinness to facilitate operative insertion in small spaces, the exterior lateral surfaces of said jaw ends being smoothly continuous and gradually tapering to a thinned nose portion which is the angled portion.

3. In an instrument as claimed in claim 1, said pivotally connected arms having strength characteristics and being so disposed with relation to the pivot position as to facilitate the cutting action and negating undesirable flexure and bending of said arms and said jaw ends.

4. In an instrument as claimed in claim 1, said jaw portions extending beyond the point of pivot of the arms and each being similarly downwardly matingly curved toward the free ends thereof, said substantial angled disposition to the plane of opening of said arms facilitating insertion and operation of instrument in areas and regions of difficult recess or where said retention pins have been bent intentionally or otherwise.

5. In an instrument as claimed in claim 1, said jaw ends respectively having a thickness of 1.5 millimeters or less with the coacting ends totalling a thickness of approximately three millimeters to permit operative insertion of the jaw ends between retention pins spacedly mounted a distance apart of approximately three millimeters.

6. In an instrument as claimed in claim 1, wherein at least one said jaw end is removable from a jaw for replacement by another.

7. In an instrument as claimed in claim 1, wherein said mating half cups and jaw ends are heat treated for increased hardness and cutting abilities.

8. In an instrument as claimed in claim 2, one said mating half cup on one said jaw end having a first flat peripheral edge surrounding said half cup shaped depression and constituting one half of compressive wire cutting means of said instrument.

9. In an instrument as claimed in claim 8, the other of said mating half cups on the other of said jaw ends having a flat peripheral edge surrounding the half cup shaped depression thereon, constituting a second half of the compressire wire cutting means by coaction between said edges and forming therebetween sealing and closing mating edges for the opposed half cups to thereby form the said closed cup shaped wire end retention means.

10. In an instrument as claimed in claim 8, the other of said mating half cups on the other of said jaw ends having a sharpened end tip section in said peripheral edge to facilitate severing a said retention pin therebetween and said first flat peripheral edge, said sharpened end section extending substantially 180° around said tip section to facilitate angular insertion and operation of said instrument in areas or regions of decreased accessibility or where said pins are bent or otherwise angled or aligned on the natural tooth portion to facilitate placement and engagement thereon of the tooth restorative material.

11. In an instrument as claimed in claim 6, wherein means are provided for operatively associating the removable jaw end and jaw and means for securing the portions together.

12. In an instrument as claimed in claim 2, each said mating half cup having sharpened cutting peripheral edges thereon.

* * * * *